(12) United States Patent
Martz

(10) Patent No.: US 6,270,275 B1
(45) Date of Patent: Aug. 7, 2001

(54) SPONGE STORAGE AND DISINFECTING DEVICE

(76) Inventor: Jasun Martz, 666 Fifth Ave., PMB 339, New York, NY (US) 10103

( * ) Notice: Subject to any disclaimer, the term of this patent is extended or adjusted under 35 U.S.C. 154(b) by 0 days.

(21) Appl. No.: 09/318,190

(22) Filed: May 25, 1999

(51) Int. Cl.[7] .................................................... B43M 11/06
(52) U.S. Cl. ....................... 401/207; 401/131; 15/257.05; 206/207
(58) Field of Search ............................. 401/207, 88, 131; 15/257.05, 257.06, 257.075, 104.92, 244.4; 220/501, 502, 531; 206/205, 207, 209

(56) References Cited

U.S. PATENT DOCUMENTS

| | | | |
|---|---|---|---|
| 496,695 | * | 5/1893 | McClung ........................... 15/257.05 |
| 593,480 | * | 11/1897 | Lewis ................... 15/257.05 |
| 4,189,802 | | 2/1980 | Lansbergen . |
| 4,674,903 | | 6/1987 | Chen . |
| 4,831,681 | * | 5/1989 | Puder ................. 15/257.05 |
| 4,847,089 | | 7/1989 | Kramer . |
| 4,866,806 | | 9/1989 | Bedford . |
| 5,507,414 | | 4/1996 | Ong . |
| 5,678,733 | | 10/1997 | Ong . |
| 5,722,537 | * | 3/1998 | Sigler .................................. 206/205 |

FOREIGN PATENT DOCUMENTS

0019593  *  5/1980  (EP) .
0074933  *  5/1980  (EP) .

* cited by examiner

Primary Examiner—Gregory L. Huson
Assistant Examiner—Peter deVore
(74) Attorney, Agent, or Firm—Thomas M. Freiburger

(57) ABSTRACT

A sponge storage and disinfecting device encloses a kitchen or bathroom sponge when not in use. The device has a housing with a hinged lid to cover the sponge container tray, and with a liquid reservoir behind the tray for dispensing a cleaning and disinfecting solution into the sponge when the sponge is pushed down in the tray. In a preferred embodiment the sponge rests on a platform supported resiliently in the tray, and pushing down of the sponge and tray opens a valve door to admit disinfecting liquid from the storage reservoir into the tray.

7 Claims, 5 Drawing Sheets

SPONGE STORAGE AND DISINFECTING DEVICE

BACKGROUND OF THE INVENTION

This invention concerns household or commercially-used sponges employed to clean countertops, cutting boards, sinks, dishes and other areas where the spread of microbes should be controlled. Specifically the invention relates to an enclosure for such sponges wherein a cleaning and disinfecting solution is conveniently dispensed to the sponge and where the sponge is isolated from airborne microbes when not in use.

Sponges have been used for over a century in household cleaning and other cleaning or wiping tasks. These include natural and synthetic sponges, typically used in domestic and commercial kitchens and baths for cleaning purposes.

A wet or damp sponge provides fertile ground for harboring and growing bacteria and other harmful microbes. Most people are unaware that the household sponge carries a number of germs that can cause diseases, particularly the bacteria salmonella, *E. coli*, staphylococcus, streptococcus and others. Clinical studies have shown that millions of children and adults become ill with stomach flu and food poisoning often occasioned by microbes spread by kitchen sponges onto countertops, cutting boards, silverware, dishes and food. Prior to this invention the only ways in which to kill or limit bacteria growth on a sponge have been to soak a sponge in a mix of potentially harmful bleach and water in the sink, to repeatedly subject the sponge to microwave energy, to wash the sponge in hot dishwater, to spray antibacterial aerosol products on the sponge, generating potentially harmful fumes, or to repeatedly change the sponge. Dish detergent in its self does not kill and prevent growth of bacteria in a wet or damp sponge.

Various sponges, detergent dispensers and related products are shown in the following patents: 4,189,802, 4,674,903, 4,847,089, 4,866,806, 5,507,414 and 5,678,733. Some of the patents involve sponges with embedded detergent or disinfecting solutions. Others concern storage of a sponge in a position for convenient dispensing of liquid cleaning substances such as dishwashing detergents into the sponge.

There has been a need for a better system to store a kitchen or bath sponge, particularly for household use, in a way which prevents or greatly reduces contamination by microbial agents and which actually serves to dispense a liquid detergent and disinfecting agent into the sponge so that the sponge can be used to disinfect various surfaces.

SUMMARY OF THE INVENTION

This invention provides a system answering the above needs, via a sponge storage and disinfecting device which houses the sponge in a closed area when not in use, and which dispenses liquid detergent/antiseptic solution into the sponge when the housing is opened and the sponge is lightly pushed down in the storage tray. This disinfects the sponge and makes it ready for use in cleaning and disinfecting surfaces.

In one embodiment the device of the invention comprises a housing with a fillable liquid reservoir for containing a disinfectant detergent liquid, preferably at the back of the housing. The reservoir has an upper fill opening and a liquid dispensing outlet located in a low position in the reservoir, adjacent to the sponge tray. The sponge tray, also formed by the housing, has sides and a bottom for containing at least one sponge. Means are provided for wetting the sponge with the liquid from the reservoir. To protect the sponge from airborne microbes and to prevent evaporation of the liquid and prevent UV ray damage to the sponge, an openable lid is provided on the housing.

In one preferred embodiment the sponge wetting means comprises a normally closed valve at the liquid dispensing outlet between the reservoir and the tray, and the sponge resides on a resiliently supported platform in the tray. When the sponge is pushed down, the platform moves down and engages against the valve to open it, admitting liquid into the tray. The sponge platform in a specific embodiment is supported on compression coil springs engaged between the platform and the tray floor.

The sponge itself preferably has three separate layers of different materials, including an abrasive layer, a highly absorbent middle layer and a durable and absorbent bottom layer.

It is thus a principal object of the invention to reduce bacterial contamination in household or commercially used sponges so that the microbes are not distributed to countertops, cutting boards and other surfaces, through a sponge container and disinfecting device which is conveniently used and unobtrusive on a countertop. These and other objects, advantages and features of the invention will be apparent from the following description of a preferred embodiment, considered along with the accompanying drawings.

DESCRIPTION OF PREFERRED EMBODIMENTS

Figure 1:
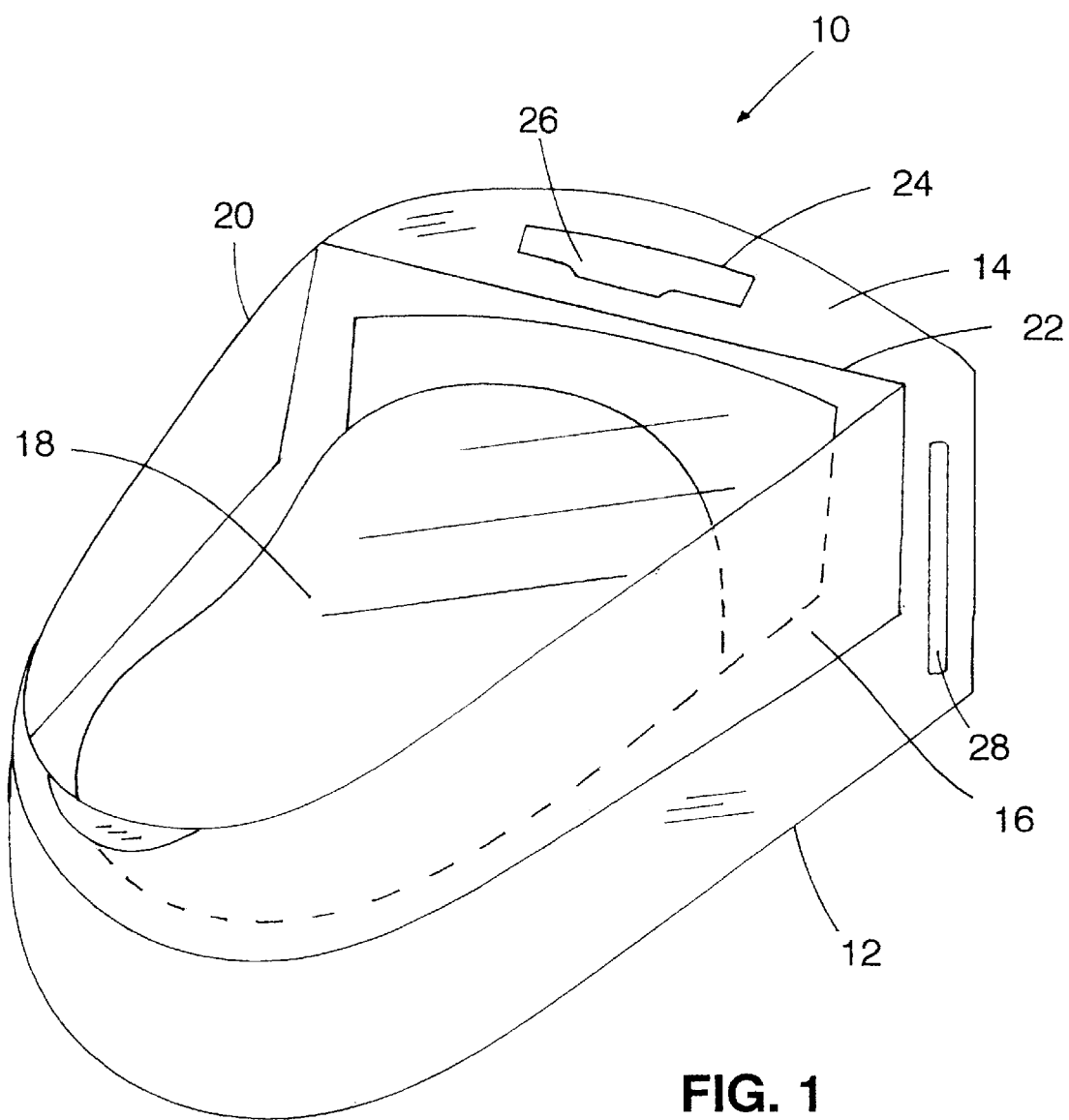
FIG. 1 is a perspective view showing a sponge container and disinfecting device of the invention, with a single sponge.

FIG. 1 shows a sponge storage and disinfecting system 10, comprising a housing 12 that forms a liquid reservoir 14 at its back end and which is shaped to define a sponge container tray 16 as shown. A sponge 18 is shown contained within the housing, and a preferably transparent or translucent plastic openable lid 20 encloses the sponge and substantially prevents contamination by airborne bacteria, as well as preventing evaporation of the liquid detergent/disinfectant. Preferably the lid 20 is hinged or pivoted along a rear hinge axis 22. The drawing also shows an upper fill opening 24 for liquid detergent/disinfectant to be added to the liquid reservoir 14, the fill opening being covered by a dispenser closure lid 26. Again, the lid 26 can be hinged if desired. The drawing also shows a liquid level viewing window 28 preferably included in the side of the liquid reservoir 14.

Figure 2:
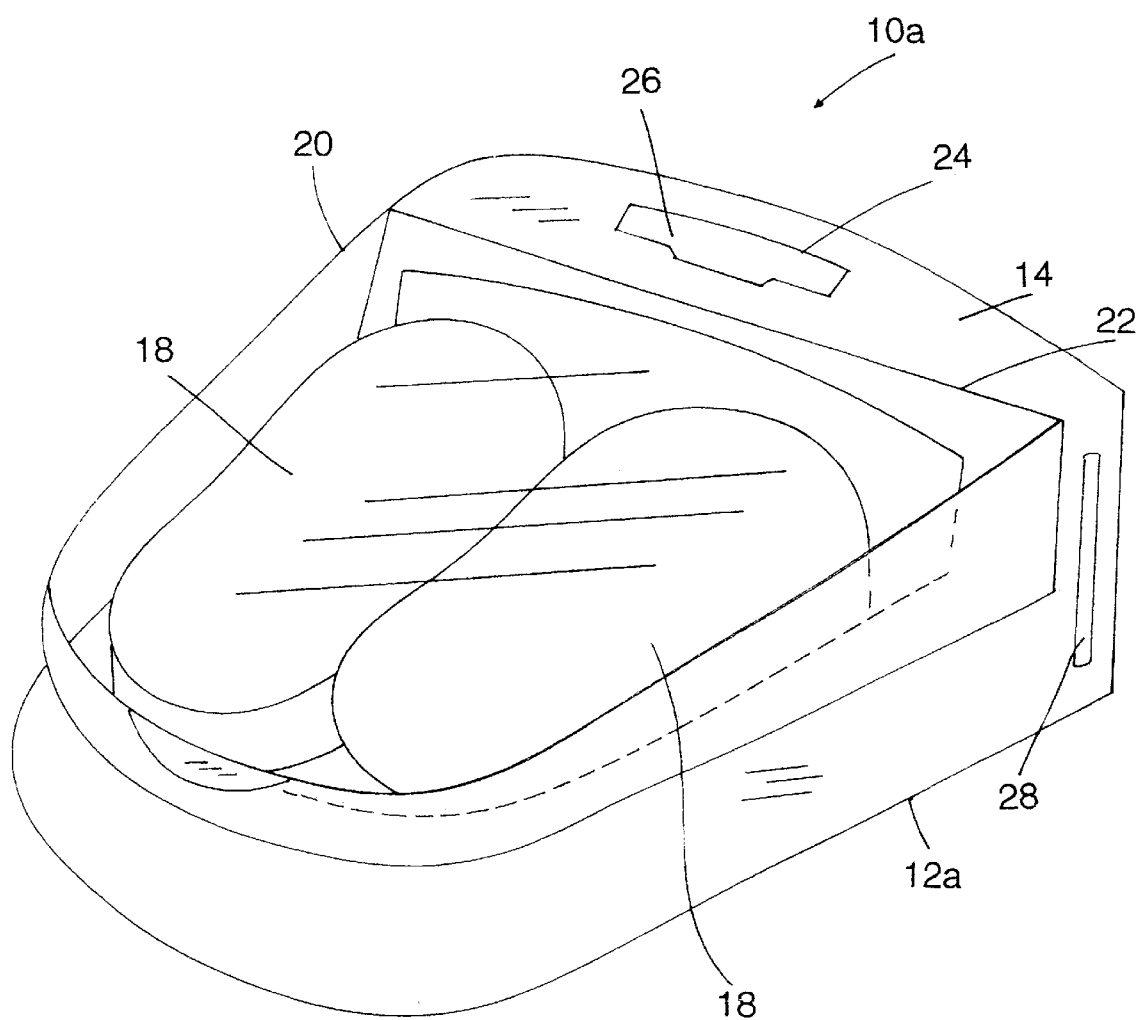
FIG. 2 is a perspective view similar to FIG. 1, but showing a larger container/disinfecting unit containing two sponges.

FIG. 2 shows a similar system 10*a*, but with the housing somewhat wider and storing two sponges 18. The construction is similar to that of FIG. 1, the principal exception being that the housing or container body 12*a* is wider.

Figure 3:
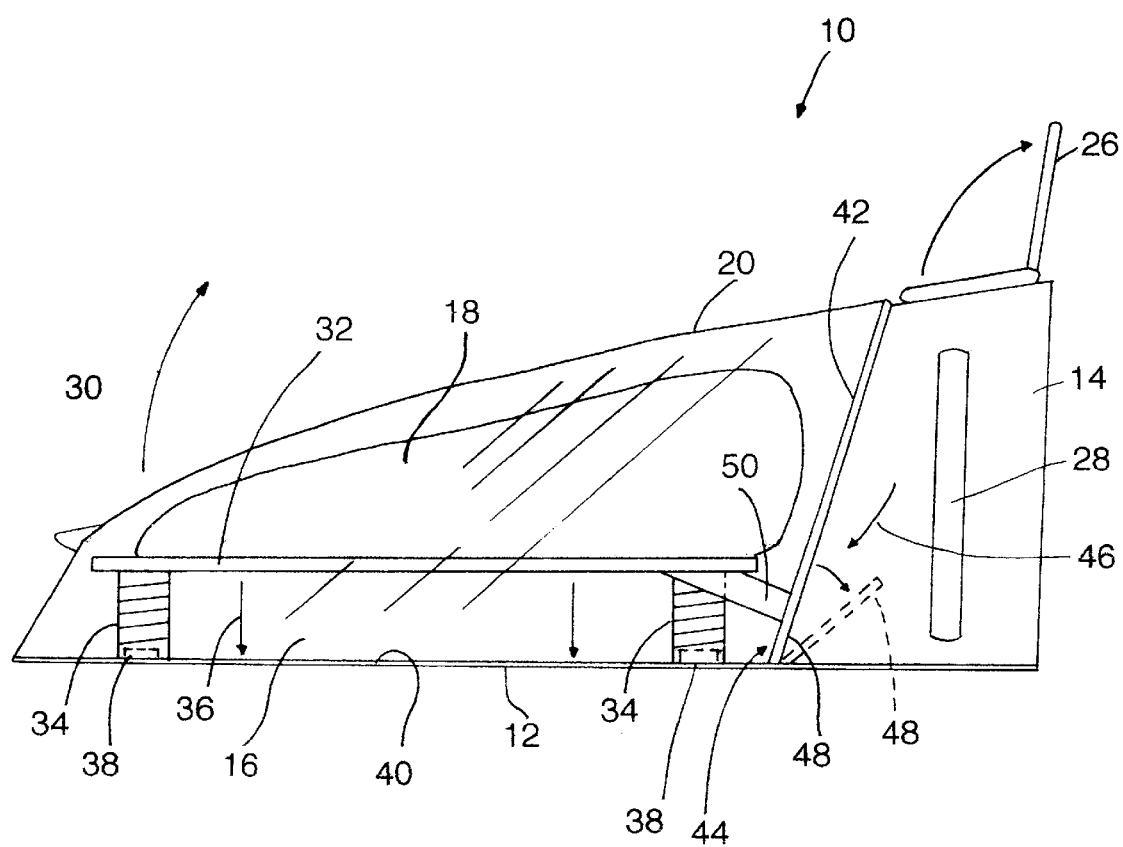
FIG. 3 is a schematic side elevation view in section, showing the device.

In FIG. 3 the housing 12 (or 12a) is shown in side view, in a schematic section which is partially not in section. The reservoir window 28 is shown in the back end of the unit 10, with the reservoir fill lid 26 in the open position for addition of detergent/disinfectant. The closure lid 20 is shown in the closed position, with an arrow 30 indicating the direction of movement to the open position. The sponge 18 is shown within the sponge container tray 16, and the sponge may be of a specific shape, tapered as shown. Supporting the sponge in the container tray is a sponge platform 32, preferably resiliently supported within the tray. In this embodiment compression springs 34 are shown supporting the platform resiliently, such that it can be pushed down with light to moderate pressure, as indicated by arrows 36. To retain the springs 34 in position, bosses 38 may be provided, extending up from the bottom surface 40 of the sponge container tray as indicated.

The liquid reservoir 14 is divided from the sponge container area by a wall 42. Within this dividing wall is a valve 44 which is normally closed but which when opened will admit liquid into the sponge container tray as indicated by the arrow 46. In this preferred embodiment, the normally closed valve comprises a pivoted flap or door 48, shown in closed position in solid lines in FIG. 3 and in open position in dashed lines. The door 48 is normally held closed by a spring (not shown) or simply by hydraulic pressure of the liquid contained within the liquid reservoir 14.

Figure 4:
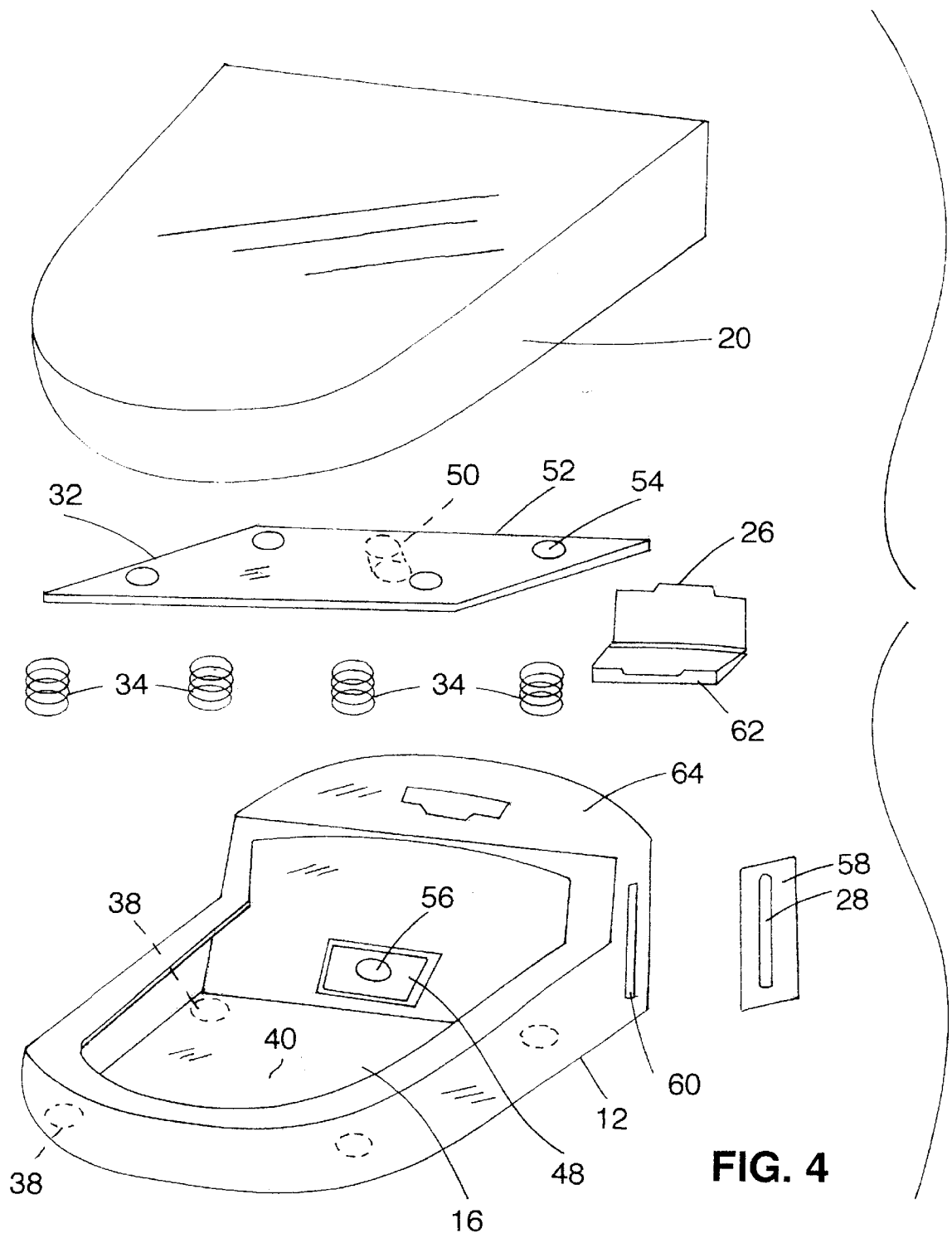
FIG. 4 is an exploded view in perspective showing components of the sponge container and disinfecting system.

FIGS. 3 and 4 show that in this preferred embodiment the pushing down of the sponge and the sponge platform 32 is effective to open the door or flap valve 44. This is caused by an extension or tail 50 fixed to the platform 32 at its back end as shown, and slidable relative to the flap or door 48. When the platform 32 is pushed down, the extension 50 rides down against the angled door 48 and opens the door in camming fashion. Alternatively, the flap 48 itself could have a boss on its forward side, angled and engagable by a back edge 52 of the platform.

FIG. 4 shows the various components of the system in exploded view. The transparent lid 20 is shown removed from the housing or body 12, and the sponge platform 32 is shown removed from the sponge container tray 16 of the housing. As noted above, in this embodiment the bottom 40 of the container tray preferably has bosses 38 for engaging and retaining in place the compression springs 34. These can be formed directly in the plastic bottom by injection molding. Preferably the springs 34 fit tightly over the cylindrical bosses 38, positively holding the springs in place. At the tops of the springs, they may be retained to the platform 32 by cylindrical recesses 54 extending up into the platform 32 from the bottom. The platform extension or tail piece 50 is shown in dashed lines in FIG. 4, extending below and angled back from the sponge platform 32. On the valve door or flap 48 is shown a spot 56 which is normally contacted by the tail or extension 50, in the normally closed position of the flap. The camming action of the extension 50 slides the contact point down from the spot 56 as the platform is pushed down, as explained above.

FIG. 4 also shows that a transparent molded plastic plate 58 may be secured over a fill indicator slot 60 to form the level indicating window 28. Also, the liquid reservoir lid 26 is shown separated from the housing, comprising the hinged lid fitted on a collar 62 which is secured to the top surface 64 of the reservoir upon assembly.

The arrangement for admitting liquid detergent/disinfecting solution into the sponge container tray from the reservoir is one example and is not intended to be limiting.

The system can, if desired, involve a reservoir whose level is kept low, with capillarity of the sponge itself serving to draw liquid into the sponge and thus ultimately to move the liquid from the reservoir into the tray. The normally closed valve 44 could be configured to have a larger surface area on the side facing the tray, with the tray arranged such that simply placing the sponge in the tray and pushing down at the back of the sponge will open the flap or door to admit liquid. Other arrangements are also possible.

Figure 5:
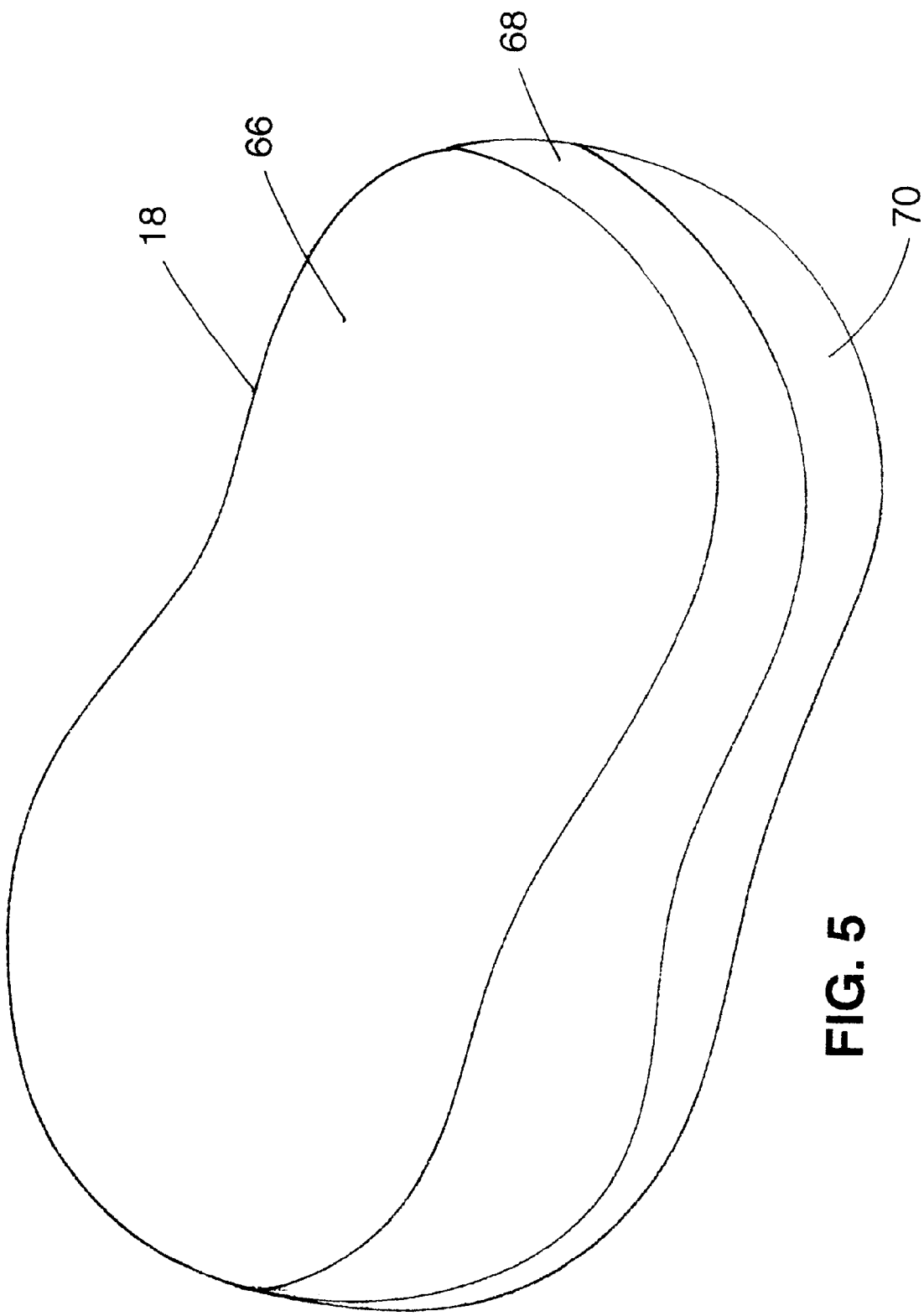
FIG. 5 is a perspective view showing a preferred embodiment of a sponge which can be used with the container device of the invention.

FIG. 5 shows one preferred embodiment of a sponge 18 which can be used with and can be a part of the system of the invention. The sponge includes three layers formed of different materials, and these can include an abrasive top layer 66, which is an important design function since it can be used, by inverting the sponge, to scour surfaces, a highly absorbent middle layer 68 which could be made from an exceptionally porous material such as poly vinyl alcohol to retain a high volume of liquid; and a highly abrasion resistant/durable absorbent bottom layer 70 that in a preferred embodiment could be made of material that does not deteriorate (like most commercially manufactured sponges) with excessive use, friction or age.

The detergent/disinfectant solution can be any of a number of effective solutions for this purpose. One solution used commonly in antibacterial cleaning and disinfecting 1 to 3% n-Alkyl (50% c14, 40% c12, 10% c16), with 97 to 99% inert ingredients.

The above described preferred embodiments are intended to illustrate the principles of the invention, but not to limit its scope. Other embodiments and variations to this preferred embodiment will be apparent to those skilled in the art and may be made without departing from the spirit and scope of the invention.

I claim:

1. A sponge storage and disinfecting device, for isolating and disinfecting a sponge used for cleaning while also supplying a cleaning detergent/disinfectant in the sponge so that the sponge is ready for use in cleaning and disinfecting surfaces, comprising:
    a housing,
    a fillable liquid reservoir in the housing for a disinfectant detergent liquid, the reservoir having an upper fill opening with a closeable lid and having a liquid dispensing outlet at a low position in the reservoir, and the liquid reservoir containing such a disinfecting detergent liquid,
    a sponge container tray forming part of the housing and being adjacent to the liquid dispensing outlet of the reservoir, the tray having sides and a bottom and containing at least one wet sponge,
    sponge wetting means for providing liquid from the liquid reservoir in the sponge container tray to wet the sponge therein, and
    man openable lid covering the sponge container tray.

2. A sponge storage and disinfecting device, for isolating and disinfecting a sponge used for cleaning while also supplying a cleaning detergent/disinfectant in the sponge so that the sponge is ready for use in cleaning and disinfecting surfaces, comprising:
    a housing,
    a fillable liquid reservoir in the housing for a disinfectant detergent liquid, the reservoir having an upper fill opening with a closeable lid and having a liquid dispensing outlet at a low position in the reservoir, and the liquid reservoir containing such a disinfecting detergent liquid, a sponge container tray forming part of the housing and being adjacent to the liquid dispensing outlet of the reservoir, the tray having sides and a bottom and containing at least one wet sponge, sponge wetting means for providing liquid from the liquid reservoir in the sponge container tray to wet the sponge therein, and an openable lid covering the sponge container tray, hinged at a back end of the openable lid.

3. A sponge storage and disinfecting device, for isolating and disinfecting a sponge used for cleaning while also supplying a cleaning detergent/disinfectant in the sponge so that the sponge is ready for use in cleaning and disinfecting surfaces, a fillable liquid reservoir in the housing at a back of the device, extending higher than the sponge container tray, for a disinfectant detergent liquid, the reservoir having an upper fill opening with a closeable lid and having a liquid dispensing outlet at a low position in the reservoir, and the liquid reservoir containing such a disinfecting detergent liquid, a sponge container tray forming part of the housing and being adjacent to the liquid dispensing outlet of the reservoir, the tray having sides and a bottom and containing at least one wet sponge, sponge wetting means for providing liquid from the liquid reservoir in the sponge container tray to wet the sponge therein, and an openable lid covering the sponge container tray.

4. The device of claim 3, wherein the sponge wetting means comprises a normally-closed valve at the liquid dispensing outlet of the reservoir, the valve being opened to cause a flow of liquid toward the sponge container tray in response to a pushing down of the sponge in the tray.

5. The device of claim 4, wherein the sponge container tray includes a sponge platform resiliently supported in the tray above the bottom of the tray, the platform having an extension positioned to open the normally closed valve when a sponge and the sponge platform are pushed down into the tray.

6. The device of claim 5, wherein the valve comprises a spring loaded closure door between the liquid reservoir and the sponge container tray, the extension of the platform being positioned to contact and push open the closure door against a spring pressure when the platform is pushed down, thus admitting liquid to the sponge container tray for absorption by a sponge carried on the platform.

7. The device of claim 5, including compression coil springs supporting the sponge platform and engaged between the tray floor and the sponge platform, providing resilient support for the sponge platform.

* * * * *